US006230551B1

(12) United States Patent
Burniston

(10) Patent No.: US 6,230,551 B1
(45) Date of Patent: May 15, 2001

(54) EVALUATION OF PARTICULATE CONTAMINANTS

(75) Inventor: Ian Burniston, Hampshire (GB)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 09/230,723

(22) PCT Filed: Jul. 23, 1997

(86) PCT No.: PCT/GB97/02001

§ 371 Date: Oct. 12, 1999

§ 102(e) Date: Oct. 12, 1999

(87) PCT Pub. No.: WO98/04901

PCT Pub. Date: Feb. 5, 1998

(30) Foreign Application Priority Data

Jul. 29, 1996 (GB) .................................................. 9615848

(51) Int. Cl.$^7$ .......................... G01N 15/06; G01N 01/24; G01N 11/02; G01N 15/00; B01D 35/143

(52) U.S. Cl. .................... 73/61.73; 73/863.23; 73/61.64; 73/864.71; 422/82; 422/101; 210/340

(58) Field of Search ................................. 73/61.71, 61.72, 73/61.73, 28.01, 28.03, 28.04, 61.64, 61.67, 863.23, 865.5, 864.71; 422/82, 73, 101; 210/340

(56) References Cited

U.S. PATENT DOCUMENTS 3,669,542 * 6/1972 Capellaro .............................. 356/36
3,837,216 * 9/1974 Shinohara ............................ 73/61 R (List continued on next page.)

FOREIGN PATENT DOCUMENTS

| 408758 A1 | 1/1991 | (EP) . |
| 0 448 837 | 10/1991 | (EP) . |
| 2 672 995 | 8/1992 | (FR) . |
| WO 96/03634 | 2/1996 | (WO) . |

*Primary Examiner*—Hezron Williams
*Assistant Examiner*—David J. Wiggins
(74) *Attorney, Agent, or Firm*—Leydig, Voit & Mayer, Ltd.

(57) ABSTRACT

A component is washed with a fluid to release particulate contaminant. The particulate-containing fluid is passed through a screen (22) having a known number of apertures of identical known size. The change in pressure caused by the accumulation of particles in the screen is measured and compared with the pressure when the screen is clean. From this, a control system (54) determines the number of particles in the fluid having a size greater than the aperture size. This is related to a unit volume by measuring the volume of fluid passing through the screen (22). If the screen blocks before all the fluid is passed through the screen (22), the fluid is pulsed in forward and reverse flow to re-distribute the particles on the screen. The fluid is then back washed from the screen to a second screen (28) having a known number of apertures of identical size. The number of particles per unit volume having a size greater than the size of the apertures of the second screen is then determined. If the second screen (28) blocks, the second screen (28) is pulsed and the fluid back washed to a third screen (32) having a known number of apertures of identical size. The number of particles per unit volume having a size greater than the size of the third screen (38) is then determined. These values are displayed by the control system (54).

41 Claims, 5 Drawing Sheets

U.S. PATENT DOCUMENTS

Figure 1:
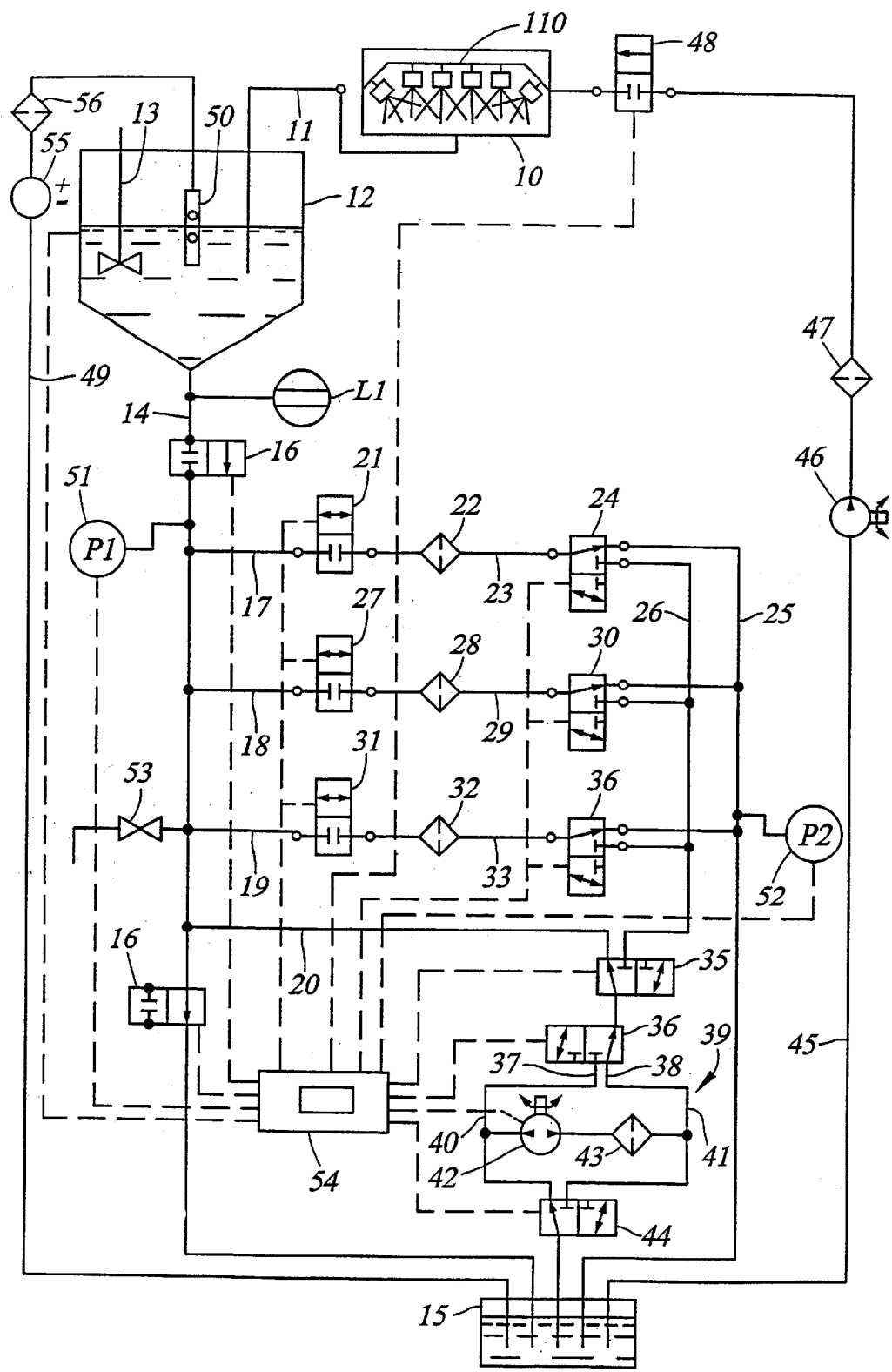

| | | | |
|---|---|---|---|
| 3,872,012 | * 3/1975 | Endicott | 210/297 |
| 4,181,009 | * 1/1980 | Williamson | 73/61.4 |
| 4,389,879 | * 6/1983 | Bach et al. | 73/61 R |
| 4,392,110 | * 7/1983 | El-Menshawy et al. | 324/453 |
| 4,492,921 | * 1/1985 | Sandulyak et al. | 324/204 |
| 4,583,396 | * 4/1986 | Hunt et al. | 73/61 R |
| 4,661,249 | * 4/1987 | Langley | 210/266 |
| 4,685,066 | * 8/1987 | Hafele et al. | 364/509 |
| 4,765,963 | * 8/1988 | Mukogawa et al. | 422/68 |
| 4,786,473 | * 11/1988 | Mukogawa et al. | 422/68 |
| 4,936,986 | * 6/1990 | Tarves, Jr. | 210/321.64 |
| 4,973,406 | * 11/1990 | Ponzielli | 210/333.1 |
| 4,977,517 | * 12/1990 | Gibbs, Jr. et al. | 364/510 |
| 5,046,355 | * 9/1991 | Tack et al. | 73/61.4 |
| 5,095,740 | 3/1992 | Hodgson et al. | 73/61 R |
| 5,198,116 | * 3/1993 | Comstock et al. | 210/636 |
| 5,266,495 | * 11/1993 | Lapidus | 436/63 |
| 5,298,161 | * 3/1994 | Sieg | 210/321.78 |
| 5,369,981 | 12/1994 | Merz et al. | 73/28.01 |
| 5,385,043 | * 1/1995 | Fitch et al. | 73/61.73 |
| 5,450,744 | * 9/1995 | Martyn | 73/61.71 |
| 5,770,152 | * 6/1998 | Schuster et al. | 422/73 |

* cited by examiner

EVALUATION OF PARTICULATE CONTAMINANTS

The invention relates to a method of evaluating particulate contaminants and to a contamination monitor.

While many mechanical components appear "clean" they are not, as a result of their production processes, completely clean. Often many of the surfaces of a mechanical component will be covered in particulates of various sizes.

Where, for example, a component is to be used in a fluid flow system, there is the possibility of the fluid picking up such particles and carrying them elsewhere in the system. In certain applications, such as in the field of electronically controlled systems or where close tolerances are a critical factor, the presence of particulate contamination can damage the system.

As a result of this, there is a need to test mechanical components to determine the size and number of particulate contaminants on the component.

It has previously been proposed to collect particulate contamination for evaluation by the following methods. In a first method, the component is filled with clean fluid and then agitated for a set period of time. The fluid is then drained from the component and will contain particulate removed from the component. In a second method, the component is installed in a purpose-built pre-cleaned test rig and fluid circulated through the component for a set period of time. Again, the particulate will be transferred to the fluid.

The particles in the fluids produced by either method are then analysed. A first method of analysis involves using an optical counting microscope to view the particles in the fluid and assess their size and number. This is, however, time-consuming and it is not possible to apply this method to all of the fluid. Accordingly, local variations in particles in the fluid can produce misleading results. The method is also labour intensive.

A second method is to pass the fluid between a light source and a sensing cell and measure with the cell interruption of the light source to count the particles. This, however, can give uncertain results with multiphase fluids where, for example, water droplets in oil are counted as particles; with fluids with entrained air bubbles when the air bubbles can be counted as particles, with opaque fluids and with fluids with high particle concentrations where particles overlap on the light sensor and are counted as one larger particle. In addition, the light source and the sensing cell are mounted in a narrow flow channel and large particles can become lodged in the channel causing downtime.

A third method is gravimetric analysis. This is, however, well known as giving inaccurate results owing co the lack of clarity on particulate size or distribution.

A fourth method is to assess the particles through a microscope with an attached image analysis computer. This method, however, identifies only particle boundary outlines and does not therefore differentiate between overlapping or agglomerated particles and one large particle. Also translucent particles will not be identified.

According to one aspect of the present invention, a method of evaluating particulate contaminants in a fluid may comprise providing a flow of particulate containing fluid through a first screen. The first screen includes apertures of a single predetermined size for filtering particulate contaminants larger than the predetermined size. Further, the method comprises determining when the pressure drop across the first screen reaches a predetermined maximum corresponding to blockage of the first screen. After determination of blockage, a reverse flow of clean fluid is provided through the first screen. The reversed clean fluid with the particulate contaminants from the first screen is flowed through a second screen. The second screen includes apertures of a predetermined size greater than the predetermined size of the apertures of the first screen. The method also comprises providing a flow of the particulate containing fluid through the second screen. The greatest pressure drop during the particulate-containing fluid flow through the second screen is determined. Moreover, the method comprises providing a flow of a clean fluid without the particulate contamination through the first screen. During the clean fluid flow, the pressure drop across the first screen is measured. The method further comprises providing a flow of a clean fluid without the particulate contamination through the second screen. The pressure drop across the second screen is measured during the clean fluid flow. From the pressure drops, the number of particles in the fluid greater than the size of the apertures of the first screen and the number of particles greater than the size of the apertures of the second screen are determined.

According to another aspect of the present invention, a contamination monitor for evaluating particulate contaminants in a fluid may comprise a chamber, a screen, a pump, a pressure sensing system, and a control system. The chamber holds a fluid carrying a particulate contaminant. The screen has apertures of a single predetermined size. The pump is in fluid communication with the screen. The pressure sensing system is coupled to the screen to sense differential pressure across the screen. The control system is coupled to the pump and the pressure sensing system to pulse a flow of fluid across the screen in alternate reverse and forward directions and to determine from the pulsed flow the number of particles in the fluid greater than the predetermined size of the apertures.

According another aspect of the present invention, a method of evaluating particulate contaminants in a fluid may comprise providing a flow of particulate-containing fluid through a screen. The screen includes apertures of a single predetermined size for filtering particulate contaminants larger than the predetermined size. Further, the method comprises determining when the pressure drop across the screen reaches a steady value. The flow is pulsed across the screen in alternate reverse and forward directions. From the pulsed flow, the number of particles in the fluid greater than the size of the apertures is determined.

According to another aspect of the present invention, a method of evaluating particulate contaminants in a fluid may comprise washing an article with a fluid in a washing chamber including removing particulate contaminants from the article via the fluid. The method also comprises stirring the particulate containing fluid in a collection chamber. The method further includes flowing the particulate containing fluid through a screen. The screen includes apertures of a single predetermined size. The number of particles in the fluid greater than the size of the apertures is determined from the flow.

According to another aspect of the present invention, a method of evaluating particulate contaminants in a fluid may comprise flowing a particulate containing fluid through a screen. The screen includes apertures of a single predetermined size. The method also comprises determining from the flow the number of particles in the fluid greater than the size of the apertures. The method further comprises passing the particulate containing fluid through a filter having a pore size smaller than the size of the smallest screen aperture to a reservoir. In addition, the method comprises drawing a washing fluid from the reservoir.

According to another aspect of the present invention, a contamination monitor may comprise a chamber, a screen, at least one pump, a pressure sensing system, and a control system. The chamber holds fluid carrying a particulate contaminant. The screen includes apertures of a single predetermined size. The at least one pump provides a flow of a clean fluid without a particulate contaminant through the screen and provides a flow of the particulate containing fluid from the chamber through the screen. The pressure sensing system is coupled to the screen to generate a first signal corresponding to the pressure drop across the screen during the clean fluid flow and a second signal corresponding to the pressure drop across the screen during the particulate containing fluid flow. The control system is coupled to the pressure sensing system and the pump to pulse flow across the screen in alternate reverse and forward directions. Further, the control system is coupled to the pressure sensing system and the pump to determine from the pulsed flow the number of particles in the particulate containing fluid greater than the predetermined size.

According to another aspect of the present invention, a contamination monitor may comprise a chamber, a screen, a reservoir, a pump, and a control system. The chamber holds a fluid carrying a particulate contaminant. The chamber includes a stirring device for stirring the fluid therein. The screen has apertures of a single predetermined size. The pump is connected between the chamber and the reservoir to direct the particulate containing fluid from the chamber through the screen toward the reservoir. The control system determines from the flow the number of particles in the fluid greater than the predetermined size.

According to another aspect of the present invention, a contamination monitor may comprise a chamber, a screen, a reservoir, a pump, a control system, and a spray device. The chamber holds a fluid carrying a particulate contaminant. The screen has apertures of a single predetermined size. The pump is connected between the chamber and the reservoir to direct the particulate containing fluid from the chamber through the screen toward the reservoir. The control system determines from the flow the number of particles in the fluid greater than the predetermined size. The spray device is arranged to spray the interior of the chamber to wash off particulates as the particulate containing fluid is being pumped from the chamber.

Figure 2:
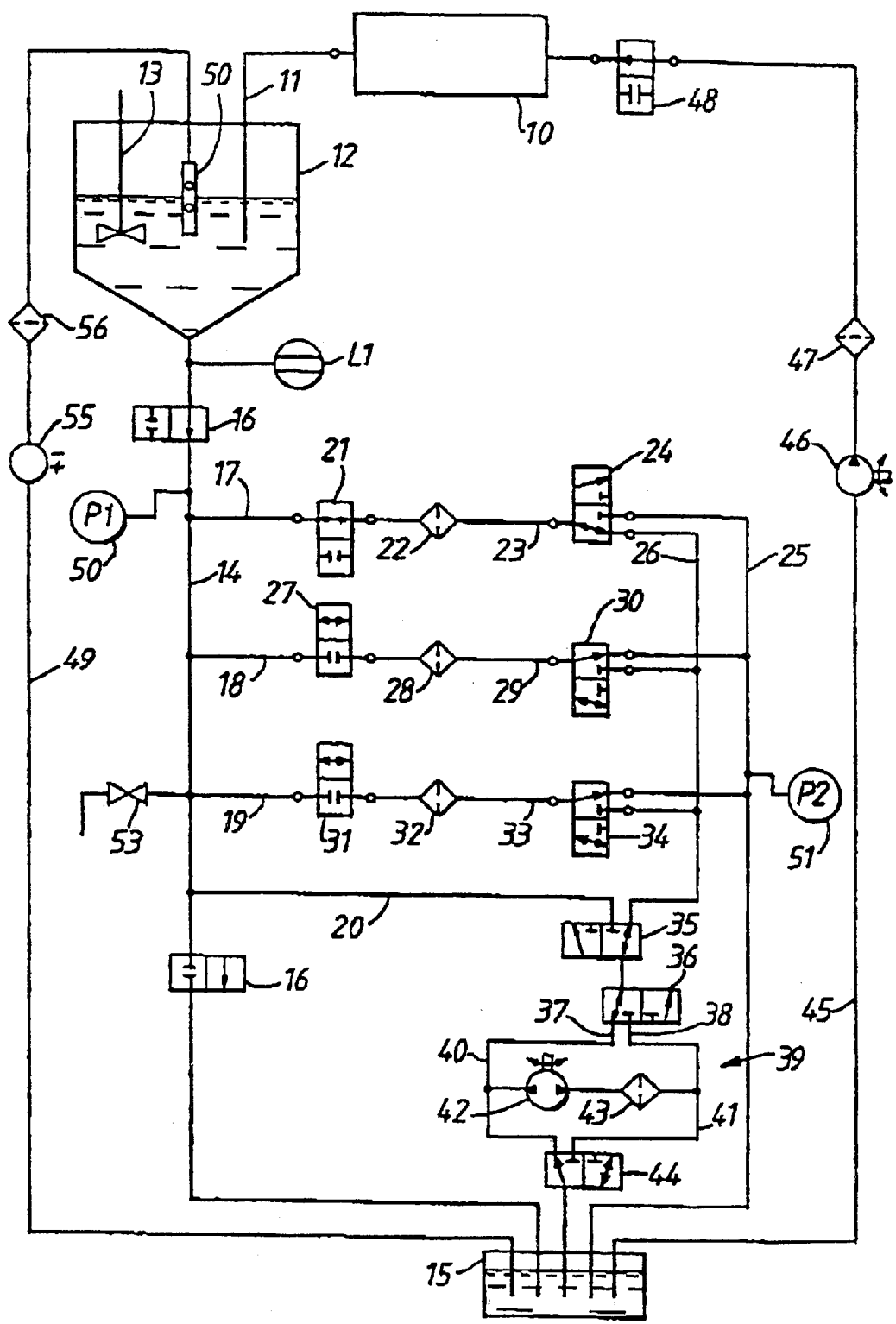
Figure 3:
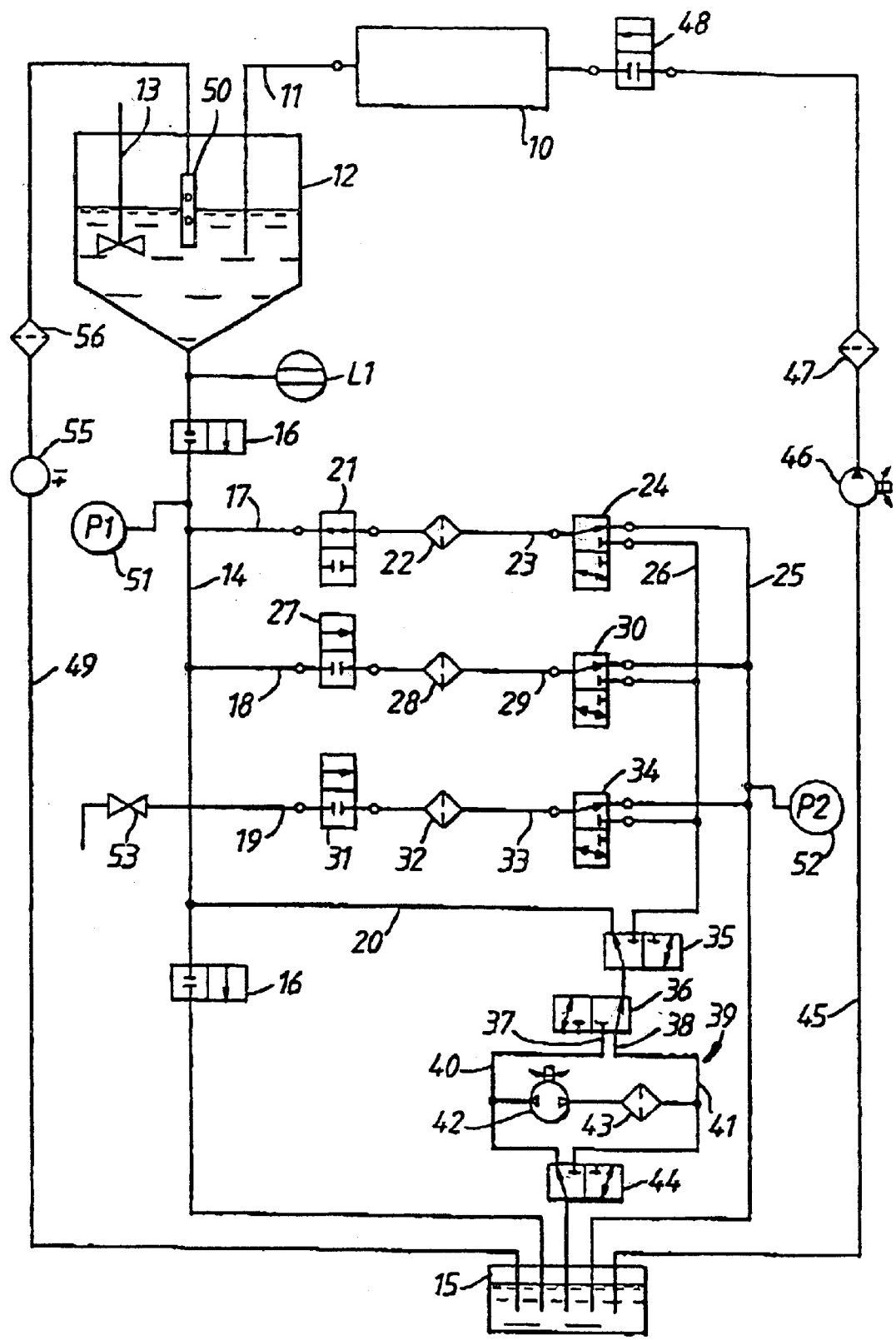
Figure 4:
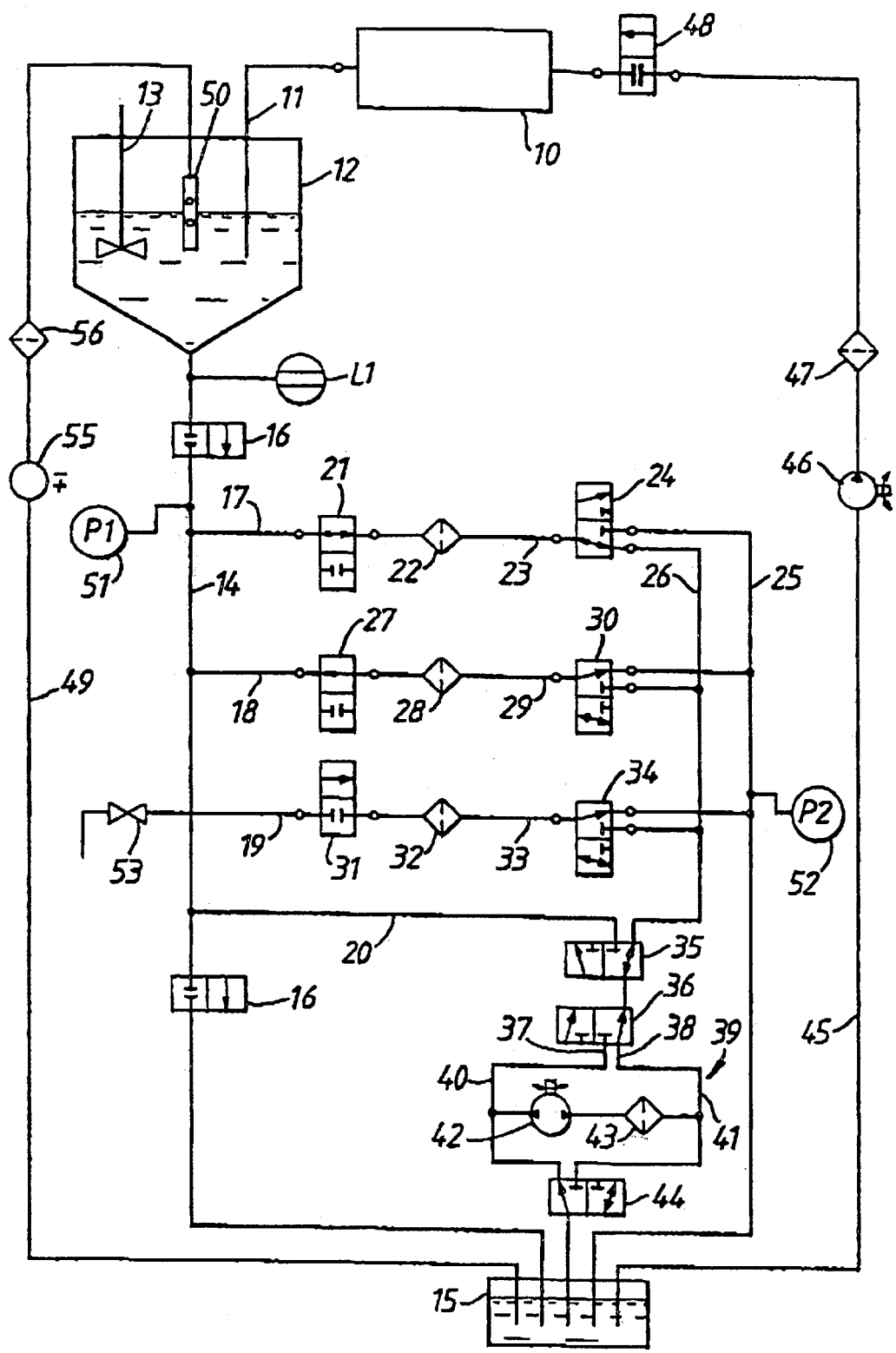

The following is a more detailed description of an embodiment of the invention, by way of example, reference being made to the accompanying drawings in which:

FIG. 1 is a diagram of a contamination monitor in a standby mode,

FIG. 2 is a similar view to FIG. 1 (with a control system omitted for clarity) but showing the monitor passing particulate-containing fluid through a first screen of the monitor, FIG. 3 is a similar view to FIG. 2 but showing the monitor arrange to measure the pressure across the first screen, and FIG. 4 is a similar view to FIGS. 2 and 3 but showing the monitor arranged to pass particulate contaminant collected on the first screen to a second screen.

Figure 5:
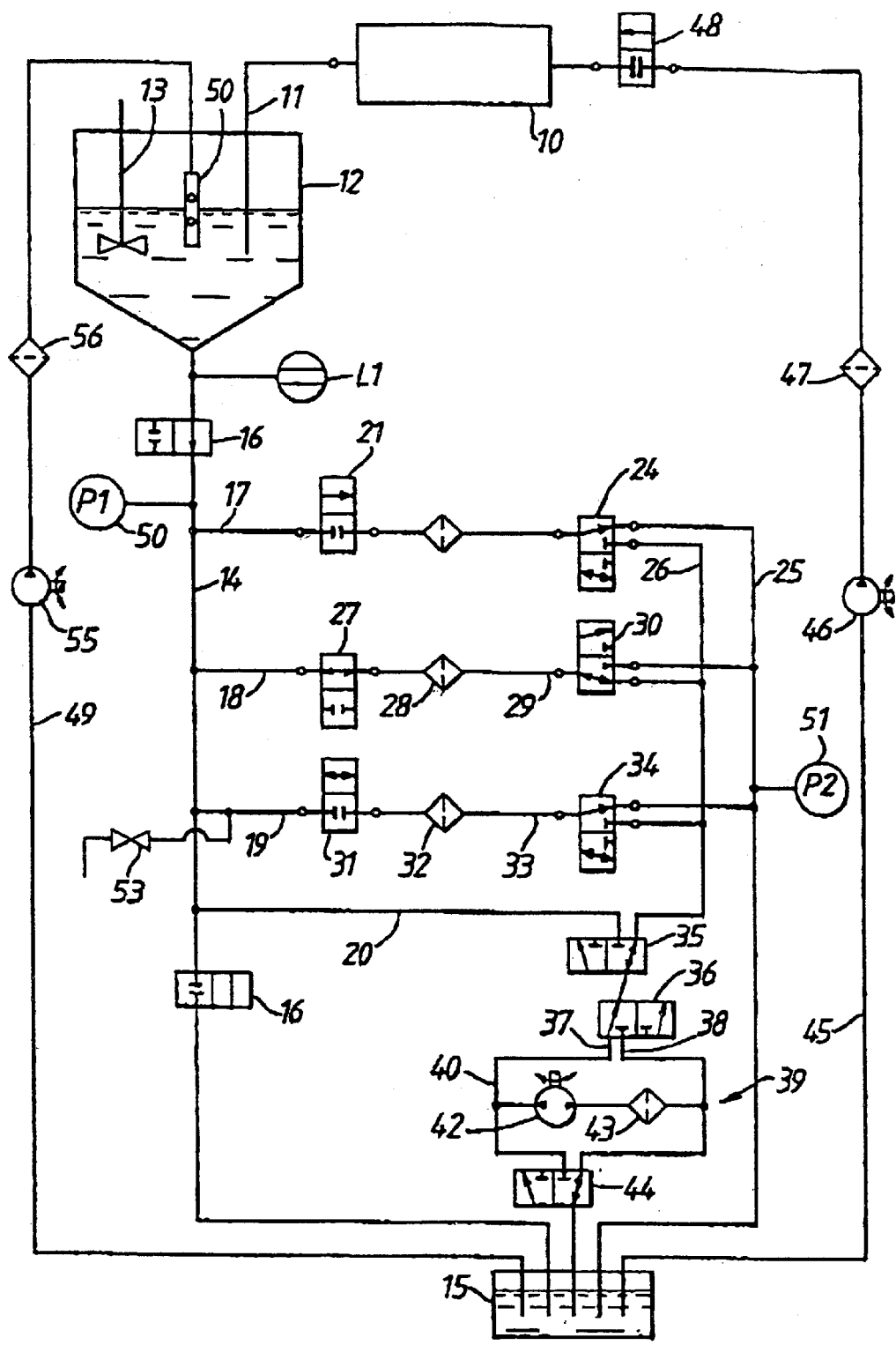

FIG. 5 is a similar view to FIG. 2 but showing the monitor arranged to pass particulate containing fluid through the second screen.

Referring first to FIG. 1, the monitor comprises a washing chamber 10 connected by a pipe 11 to a collection chamber 12. The collection chamber contains a stirrer 13.

The collection chamber 12 has an outlet pipe 14 leading to a reservoir 15. The outlet pipe 14 includes upstream and downstream on/off valves 16 respectively closer to and further from the chamber 12. Between the on/off valves 16 are four branch lines 17,18,19,20. The first branch line 17 leads via a first on/off valve 21 to a first screen 22. The first screen 22 has mesh apertures of a single predetermined size; in this case 15 $\mu$m. The number of apertures in the first screen 22 is known.

A first outlet line 23 leads from the downstream end of the first screen 22 to a first diverter valve 24 which connects the first outlet line either to a drain line 25 leading to the reservoir 15 or to a pump line whose function will be described below.

The second branch line 18 is similarly arranged to the first branch line 17 with a second on/off valve 27 in series with a second screen 28, a second outlet line 29 and a second diverter valve switching between the drain line 25 and the pump line 26. The second screen 28 has, in this embodiment, a mesh aperture of 100 $\mu$m and a known number of apertures.

The third branch line 19 is also similarly arranged with, in series along the line, a third on/off valve 31, a third screen 32, a third outlet line 33 and a third diverter valve 34 connecting to either the drain line 25 or the pump line 26. The third screen 32 has, in this embodiment, a mesh aperture size of 200 $\mu$m and a known number of apertures.

The fourth branch line 20 and the recirculating line 26 are connected to a fourth diverter valve 35 in series with a fifth diverter valve 36 which is in turn connected to first and second outlets 37,38 of a pump/filter loop indicated generally at 39. This allows either the first outlet 37 or the second outlet 38 to be connected to either the fourth branch line 20 or the pump line 26.

The pump/filter loop 39 comprises two feed pipes 40,41. The first outlet 37 is formed at the end of the first feed pipe 40 and the second outlet 38 is formed at the end of the second feed pipe 41. A gear wheel pump 42 in series with a filter 43 having a $\beta \geq 200$ at 1 $\mu$m rating. The other ends of the first and second feed pipes 40,41 are connected to a sixth diverter valve 44 which operates to connect one or other of the first and second feed pipes 40,41 to the reservoir 15.

A wash pipe 45 leads from the reservoir 15 via a second pump 46, a second $\beta \geq 200$ at 1 $\mu$m filter 47 and an on/off valve 48 to the washing chamber 10. A spray pipe 49 leads from the reservoir 15 via a pump 55 and a third $\beta \geq 200$ at 1 $\mu$m rated filter 56, to a spray head 50 within the collection chamber for a purpose to be described below. Two pressure sensors are provided. A first pressure sensor 51 is located upstream of the junction between the outlet pipe 14 and the first branch line 17 and a second pressure sensor 52 is connected to the third outlet line 25.

A valve controlled drain 53 is provided at the junction between the third branch line 19 and the outlet pipe 14.

The monitor also includes a control system 54 controlling the on/off valve 16,21,27,31 and 48, the diverter valves 24,30,34,35,36,44, the pumps 42,46 and 55, the stirrer 13 and the spray head 50. In addition, the control system 54 receives pressure signals from the first and second pressure sensors 51,52.

The monitor described above with reference to the drawings is for determining the size and number of particles on a mechanical component. This can be done either before or during assembly of the component. The monitor does this in the following way.

The operation commences with the monitor in the standby mode shown in FIG. 1. In this mode, the upstream on/off valve 16 in the outlet pipe 14 is closed and the downstream on/off valve 16 is open. The first, second and third on/off valves 21,27 and 31 in the first, second and third branch lines 17,18,19 are all closed. The first, second and third diverter valves 24,30 and 35 connect their respective outlet lines 23,29,33 to the drain line. The fourth, fifth and sixth diverter valves 35,36,44 are arranged to connect the reservoir to the fourth branch line 20 via the pump 42 and the filter 43.

The second pump 46 is non-operational and the on/off valve 48 in the wash pipe 45 is off. The pump 55 in the spray line 49 is also non-operational.

In this standby mode, the control system 54 operates the gear pump 42 which draws fluid from the reservoir 15, flows it through the filter 43, through the fourth branch line 20, through the downstream on/off valve 16 from where it returns to the reservoir 15. This acts to ensure that these lines and the associated valves and fluid are clean.

At the end of the clean-up cycle, the downstream on/off valve 16 is closed and the first on/off valve 21 in the first branch line 17 is opened. The pump 42 is then operated by the control system to pass fluid from the reservoir 15 through the filter and through the first screen 22 before returning it via the drain line 25 to the reservoir 15. Once steady flow has been established, the control system 54 stores the pressure readings from the first pressure sensor 51 and the second pressure sensor 52. The difference is then calculated. This difference is a measure of the pressure drop induced in the fluid by the first screen in a clean mode (i.e. without any of the mesh apertures blocked). This procedure is repeated for the second screen 28 and the third screen 32 by operation of the valves 27,31 and appropriate clean pressure readings are obtained.

The component whose particle contamination is to be measured is then placed in the washing chamber 10. The wash pipe 45 is opened by opening the associated on/off valve 48 and the control system 54 then operates the second pump 46 to pass fluid from the reservoir 15 through the second filter 47 to the washing chamber 10. Within the washing chamber 10, the component (not shown) is sprayed by a spray device 110 with fluid from various angles to ensure that all particulates are washed from the component. The second pump 46 is a gear pump and so passes the fluid at a known volume per unit time. The control system 54 monitors the time for which the second pump 46 operates and thus can determine the volume of fluid passed to the washing chamber 10.

The particulate containing fluid drains from the washing chamber 10 through the pipe 11 to the collection chamber 12. The control system 54 operates the stirrer 13 continuously to prevent any settling of the particles.

With the monitor in the standby mode shown in FIG. 1, the following operations then take place; The downstream on/off valve 16 in the outlet pipe 14 is then closed and the upstream on/off valve 16 in the outlet pipe 14 is opened. The on/off valve 21 in the first branch line 17 is then opened to connect the first screen 22 to the collection chamber 12. The first diverter valve 24 is operated to connect the first outlet line 23 to the pump line. The fourth and fifth diverter valves 35,36 are operated to connect the pump line 26 to the first outlet 37 and to connect the second feed pipe 41 to the reservoir via the pump 42 and the filter 43. This configuration is shown in FIG. 2.

In this configuration, the control system 54 operates the first pump 42. This draws the particulate-containing fluid from the collection chamber 12 through the first screen 22, through the first pump 42, through the filter 43 and into the reservoir 15. Since the first pump 42 passes a fixed volume per unit of time, the volume of fluid passed to the reservoir 15 can be calculated by measuring the time of operation of the first pump 42. Particles in the fluid are thus drawn into the apertures of the first screen 22.

As the fluid level drops in the collection chamber 12, fluid drawn from the reservoir 15 is passed through the spray pipe to the spray head 50. This washes down the sides of the collection chamber 12 to ensure that no contaminant is stuck to the sides. The volume of fluid that is sprayed into the collection chamber 12 is measured and added to the volume of fluid used for the rinsing/washing cycle. This is done on each occasion that fluid is drawn from the chamber 12.

During this cycle, the pressure downstream of the first screen 22 is measured (as the difference in the pressures from the first and second pressure sensors 51,52) by closing the upstream on/off valve 16 in the outlet pipe 14, by operating the first diverter valve 24 to connect the first outlet line 23 to the drain line 25 and by operating the fourth and fifth diverter valves 35,36 to connect the first feed pipe 40 to the reservoir 15, to close the first outlet 37 and connect the second outlet 38 to the fourth branch line 20 while closing the pump line 26. As a result of this, operation of the pump 42 passes fluid through the filter 43, through the fourth branch line 20, through the outlet pipe 14, through the screen 22 and through the drain line 25 to the reservoir 15. When steady flow has been established, the differential pressure reading from the first and second pressure sensor 51,52 is stored by the control system 54.

The control system 54 then takes the difference between the scored clean initial differential pressure signal for the first screen 22 and this differential pressure signal and computes a pressure difference value for the first screen 22.

It will be appreciated that the particles in the fluid that gather on the first screen 22 will either be insufficient to block the screen or will be sufficient to block the screen.

In the former case (partial blocking), the pressure difference will eventually stabilize to a steady value less than a value indicating that the first screen 22 is blocked. When this is sensed by the control system 54 (or after a time out function), the control system 54 then operates the monitor to give a small reverse pressure pulse across the first screen 22. The flow is then reverted back to a forward flow to give a forward pressure pulse across the first screen 22. This is repeated a further six times to give a total of seven pulses in the forward and reverse directions. This is achieved by configuring the monitor as shown in FIG. 3 and then operating the fourth diverter valve 35 to pump fluid from the reservoir 15 alternately through the fourth branch line 20. This passes fluid alternately in opposite directions through the first screen 22.

During each forward flow pulse, the differential pressure reading from the first and second pressure sensors 51,52 is stored by the control system. The pulses ensure that no single particulate has blocked off more than one mesh aperture in the first screen 22 and that particles larger than 15 $\mu$m (in this embodiment) have not trapped smaller particles.

The number of particles is determined from a look-up table in the control system which holds the correlation between the pressure difference and the number of mesh apertures in the first screen that are blocked. By precise monitoring of the pressure difference, the blocking of a very small number of apertures, even a single mesh aperture, can be determined. The control system 54 thus outputs the value of the number of particles in the fluid greater than 15 $\mu$m. By knowing the volume of fluid passed through the first screen 22 (by monitoring the rime of operation of the first pump 42) the number of such particles per unit volume can be calculated.

As mentioned above, the alternative is that the pressure difference reaches a terminal value indicating blockage of the first screen 22 before all the fluid has passed from the collection chamber 12 to the reservoir 15. If this occurs, the system commences to pulse the flow as described above. After this, the second stage of analysis commences.

For this, the monitor is configured as shown in FIG. 4. The upstream on/off valve 16 in the outlet pipe 14 is closed to prevent the passage of fluid from the collection chamber 12. The first diverter valve 24 is operated to connect the first outlet pipe 23 from the first screen to the pump line 26 and the fourth, fifth and sixth diverter valves 35,36,44 are operated so chat the first feed pipe 40 is connected to the reservoir 15 but has the first outlet 37 closed while the second feed pipe 41 is not connected to the reservoir 15 but has the second outlet 38 connected to the pump line 26. The fourth branch line 20 is closed.

The pulp 42 is then operated. This draws fluid from the reservoir 15 and passes it through the pump line 26 to backwash the first screen 22. This removes the particles from the first screen and passes them through the first on/off valve 21 and the outlet pipe 14 to the second branch line 18. The second on/off valve 27 is open allowing the particulate-containing fluid to pass to the second screen 28.

The first pump 42 continues to operate in this mode until the pressure readings from the first and second pressure sensors 51,52 indicate that the pressure differential is the same as the previously measured clean pressure of the first screen 22. The time of operation of the first pump 42 is noted to allow calculation of the volume of fluid passed in this mode. Alternatively, if the clean pressure is not reached after a predetermined time interval, the pump 42 is stopped after this time interval.

Referring to FIG. 5, when the clean pressure differential of the first screen 22 has been reached or the time interval completed, the monitor is re-configured to pump the remaining particulate-containing fluid from the collection chamber through the second screen 28. This is done by opening the upstream on/off valve 16 in the outlet pipe, closing the first on/off valve 21 in the first branch line 17, operating the second diverter valve 30 to connect the second outlet line 29 to the pump line 26 and by connecting the reservoir 15 the second feed pipe 41 and by connecting the first outlet 37 to the first feed pipe 40 to the pump line 26.

The pump 42 is then operated to draw the remaining particulate-containing fluid from the collection chamber 12 through the second screen 28 and then via the pump line 26 and the filter 43 to the reservoir 15. During this flow, the differential pressure across the second screen 30 is measured using the first and second pressure sensors 51,52 in a similar way to the measurement of differential pressure across the first screen 22 described above with reference to the drawings. This involves configuring the monitor as shown in FIG. 3 but winch the first on/off valve 21 closed, the second on/off valve 21 open and the second diverter valve 30 connected to the drain line 25.

As with the first screen 22, this monitored pressure is compared with the clean differential pressure scored in the control system 54. Also as with the first screen 22, there is one of two possibilities. Either the pressure difference between the clean differential pressure value and the second differential pressure value will reach a value indicating that the second screen 30 is blocked before all the fluid has been passed from the collection chamber 12 or it will reach a steady state value below the blocking value and will therefore time out.

In the latter case, the control system 54 will generate a pressure pulse across the second screen 30 seven times as described above to ensure that no large or fibrous particles have blocked off more than one hole. The control system 54 will also calculate the number of particles greater than 100 $\mu$m (in this embodiment) and, from the volume of fluid passed, display both the number of particles greater than 15 $\mu$m and the number of particles greater than 100 $\mu$m per unit volume of fluid.

In the former event, (when the pressure difference indicates blockage of the second screen 30), the fluid is pulsed through the second screen 30 in the same way as described above with reference to the first screen 22 but with the valves configured to pulse the second screen 30. There are seven pulses in forward and reverse directions and the second pressure is measured on each forward pulse. This again ensures that no fibres or larger particles block any of the 100 $\mu$m mesh apertures.

Next, the monitor is configured in a similar way to FIG. 4, to backwash the second screen 28 and pass the particulate-containing fluid through the third screen 32. As compared with FIG. 4, the first on/off valve 21 in the first branch line 17 is closed, the third on/off valve 31 in the third branch line 19 is opened, the second diverter valve 30 connects the second outlet line 29 to the pump line 26 and the third diverter valve 34 is as shown in FIG. 4; connecting the third outlet line 33 to the drain line 25. Operation of the pump 42 then pumps fluid from the reservoir 15 through the filter 43 and the pump line 26 and then through the second screen 28 where the particles are washed off the second screen 28, The fluid, with the particles, then passes along the second branch line and the outlet pipe, through the third branch line 19 to the third screen 32.

When the first pressure sensor 51 indicates a clean pressure reading for the second screen 28 or after a predetermined time interval has elapsed, the set-up of the monitor is altered so that the remaining fluid, if any, from the collection chamber 12 is passed through the third screen 32. This is done by closing the second on/off valve 27, opening the upstream on/off valve 16 in the outlet pipe 14, operating the third diverter valve 34 to connect the third outlet line 33 to the pump line 26 and connecting the pump filter loop 39 so that the pump draws fluid from the pump line 26 and delivers it to the reservoir 15.

During this passage, the differential pressure is monitored and compared with the clean pressure for the third screen 32.

If all the fluid is drawn from the collection chamber 12 in this step, or if the maximum differential pressure across the third screen 32 is detected, the control system 54 will commence pulsing seven times across the third screen 32 as described above. The control system 54 will calculate the number of 200 $\mu$m particles using the look-up table and the pressure difference. In this case, the control system 54 will give an output showing the number of particles greater than 15 $\mu$m per unit volume, the number of particles greater than 100 $\mu$m per unit volume, and the number of particles greater than 200 $\mu$m per unit volume.

Once the analysis has been completed, the monitor can be operated to backwash the particles held on the third screen 32 to a remote filter patch so that microscopic analysis can be conducted. Otherwise, the particles are backwashed and passed to the filter 43 with the fluid being returned to the reservoir 15. This is done by configuring the system as shown in FIG. 4 but closing the first and second on/off valves 21, 27, operating the third diverter valve 34 to connect the third outlet line 33 to the reservoir 15 and configuring the pump filter loop 39 so that the first feed pipe 40 is connected to the branch line 20 and the second feed pipe is connected to the reservoir 15. Operation of the pump 42 then draws fluid from the reservoir 15 back flows it through the third screen 32 and the diverter valves 35,36 and then passes it to the screen 42 via the associated valve 34. The filters 43,47,56 can be changed periodically.

The monitor then reverts to the standby mode described above with reference to FIG. 1. The values of the clean differential pressure are then measured for the first screen 22, the second screen 28 and the third screen 32 using the first and second pressure sensors 51,52 and are held by the control system 54. If these values differ from the values for the first test, the datum is set to the new value for the following test. This happens for each subsequent test until the screens 22,28,32 become too contaminated to perform any further tests.

As mentioned above, it is possible that, when the particles are backwashed off a filter screen, not all the particles will be removed. In the backwashing steps described above with reference to the drawings, the backwashing is continued either until the clean pressure is reached or until a particular time has elapsed. If the clean pressure is not reached before the predetermined time has elapsed, this means that the screen being backwashed is not completely unblocked.

This is not, however, a problem because, as described above, the clean pressure values are reset at the beginning of each monitoring cycle.

It will be appreciated that there are a number of modifications that can be made to the monitor described above with reference to the drawings. Although three screens 22,28,32 are described, there could be one or two or four or more screens. The screens need not have the mesh aperture sizes indicated above, they could have any desired size depending on the size of the particles likely to be encountered. The system of valves and pipes described above is nor essential; the system could be re-arranged as required to allow the determination of the pressure drop across a screen with particle containing fluid.

The monitor described above with reference to the drawings has the advantage of monitoring the entire test volume of fluid. It is automated and so requires comparatively little labour. It is not affected by multi-phase fluids and does not have particle size limitations above 5 $\mu$m. It is not affected by the presence of air or water in the fluid and is not affected by high concentrations of contaminate particles. It does not matter whether the fluid is opaque and produces results very quickly, possibly in minutes.

The pulsing of the fluid across the screens ensures that the contaminant particles are stable and evenly distributed. Since fluid samples do not need to be taken for analysis, there is no risk of extraneous handling corrupting the samples.

Since the information regarding the particle sizes per unit volume is stored by the control system, there is the possibility of down loading the information electronically to allow trends over time to be monitored. The monitor is self-diagnosing. Between each test, the monitor identifies residual blockages in the screens 22,28,32 and adjusts the starting clean pressure values to take account of such blockages.

What is claimed is:

1. A method of evaluating particulate contaminants in a fluid comprising:

providing a flow of particulate-containing fluid through a first screen having apertures of a single predetermined size for filtering particulate contaminants larger than the predetermined size;

determining when the pressure drop across the first screen reaches a predetermined maximum corresponding to blockage of the first screen;

after determination of blockage, providing a reverse flow of clean fluid through the first screen and then flowing the reversed clean fluid with the particulate contaminants from the first screen through a second screen having apertures of a predetermined size greater than the predetermined size of the apertures of the first screen;

providing a flow of the particulate-containing fluid through the second screen;

determining the greatest pressure drop during the particulate-containing fluid flow through the second screen;

providing a flow of a clean fluid without the particulate contamination through the first screen;

measuring the pressure-drop across the first screen during the clean fluid flow;

providing a flow of the clean fluid without the particulate contamination through the second screen;

measuring the pressure drop across the second screen during the clean fluid flow; and determining from the pressure drops the number of particles in the fluid greater than the size of the apertures of the first screen and the number of particles greater than the size of the apertures of the second screen.

2. A method according to claim 1 wherein providing a flow of particulate-containing fluid through the first screen includes flowing a known volume of the particulate-containing fluid through the first screen, the number of particles per unit volume being determined using the volume.

3. A method according to claim 1 further comprising pulsing flow across the first screen in alternate reverse and forward directions after determining when the pressure drop across the first screen reaches the predetermined maximum value.

4. A method according to claim 1 wherein the first screen has an aperture size of 15 $\mu$m.

5. A method according to claim 1 wherein providing a flow of particulate-containing fluid through the second screen includes flowing a known volume of the particulate-containing fluid through the second screen, the number of particles per unit volume being determined using the volume.

6. A method according to claim 1 and comprising determining when the pressure drop across the second screen reaches a steady value and then pulsing flow across the second screen in alternate reverse and forward directions, the pressure drop across the second screen being measured during each forward pulse and the number of particles being determined using an average of the forward pulse pressure drops.

7. A method according to claim 1 wherein determining the pressure drop across the second screen includes determining when the pressure drop across the second screen prior to completion of the particle-containing flow reaches a predetermined maximum corresponding to blockage of the second screen.

8. A method according to claim 1 wherein the apertures of the second screen have a size of 100 $\mu$m.

9. A method according to claim 7 comprising:

after the determination of the blockage of the second screen, providing a reverse flow of clean fluid through the second screen and then flowing the reversed clean fluid with the particulate contaminants from the second screen through a third screen having apertures of a predetermined size greater than the predetermined size of the apertures of the second screen;

providing a flow of the particulate containing fluid through the third screen; and determining from the flow the number of particles in the fluid greater than the size of the apertures of the third screen.

10. A method according to claim 9 and comprising flowing through the third screen the clean fluid without the particulate contamination, measuring the pressure drop across the third screen during the clean fluid flow and then flowing the particulate-containing fluid and measuring the greatest pressure drop during the particulate-containing fluid flow, the number of particles being determined using the pressure drops.

11. A method according to claim 10 and comprising flowing a known volume of the particulate-containing fluid through the third screen, the number of particles per unit volume being determined using the volume.

12. A method according to claim 10 and comprising:
determining when the pressure drop across the third screen reaches a steady value, and then
pulsing flow across the third screen in alternate reverse and forward directions, the pressure drop across the third screen being measured during each forward pulse to obtain a forward pulse pressure drop and the number of particles being determined using an average of said forward pulse pressure drops.

13. A method according to claim 9 wherein the size of the apertures of the third screen is 200 µm.

14. A method according to claim 1 and further comprising placing an article in a washing chamber, washing the article with a clean fluid and then utilizing the fluid after the wash as the particulate-containing fluid.

15. A method according to claim 14 and comprising passing the particulate-containing fluid to a collection chamber, flowing the particulate-containing fluid from the collection chamber and rinsing the collection chamber with the clean fluid during the flow.

16. A method according to claim 15 and comprising stirring the particulate containing fluid in the collection chamber.

17. A method according to claim 1 and comprising passing the particulate-containing fluid through a filter having a pore size smaller than the size of the smallest screen aperture toward a reservoir.

18. A method according to claim 17 wherein the filter has a $\beta \geq 200$ at 1 µm rating.

19. A method according to claim 17 further comprising drawing a washing fluid and a rinsing fluid from the reservoir.

20. A contamination monitor for evaluating particulate contaminants in a fluid comprising:
a chamber for holding a fluid carrying a particulate contaminant;
a screen having apertures of a single predetermined size;
a pump wherein the pump is in fluid communication with the screen;
a pressure sensing system coupled to the screen to sense differential pressure across the screen; and
a control system coupled to the pump and the pressure sensing system to pulse a flow of fluid across the screen in alternate reverse and forward directions and to determine from the pulsed flow the number of particles in the fluid greater than the predetermined size of the apertures.

21. A monitor according to claim 20 wherein
the pump flows through the screen a clean fluid without the particulate contamination,
the pressure sensing system feeds to the control system a first signal corresponding to the pressure drop across the screen during the clean fluid flow and a second signal corresponding to the pressure drop across the screen when the particulate-containing fluid is flowed through the screen, and
the control system determines from the signals the number of particles.

22. A monitor according to claim 21 and including a measuring device for passing to the control system a signal corresponding to the volume of particle-containing fluid passed through the screen, the control system determining from the signal the number of particles per unit volume.

23. A monitor according to claim 21 wherein
when the second signal reaches a predetermined value, the control system controls the pump to pulse the flow across the screen in alternate reverse and forward directions,
the pressure sensing system feeding the control system the second signals corresponding to the pressure drop across the screen during the forward pulses to obtain a forward pulse pressure drop, and
the control system determines the number of particles from an average of the forward pulse pressure drop signals.

24. A monitor according to claim 20 wherein the control system is coupled to the pressure sensing signal system to determine when a pressure drop across the screen corresponds to blockage of the screen, the control system then halting the pump.

25. A monitor according to claim 20 and comprising:
a reservoir,
the pump being connected between the chamber and the reservoir to direct the particulate containing fluid from the chamber through the screen toward the reservoir.

26. A monitor according to claim 25 wherein the chamber includes a stirring device for stirring fluid in the chamber.

27. A monitor according to claim 25 wherein the fluid is flowed to the reservoir through a filter having a pore size smaller than the aperture size of the screen.

28. A monitor according to claim 27 wherein the filter has a $\beta \geq 200$ at 1 µm rating.

29. A monitor according to claim 25 and including a washing chamber for receiving an article, fluid from the reservoir washing the article, and then passing the fluid containing the particulates from the article to the chamber.

30. A monitor according to claim 29 wherein the washing chamber includes a spray device arranged to spray the interior of the washing chamber to wash off particulates as the particulate-containing fluid is being pumped from said washing chamber.

31. A monitor according to claim 29 wherein
at least one further screen is connected between the washing chamber and the reservoir in parallel with the first-mentioned screen,
the at least one further screen having an aperture size greater than the first-mentioned screen,
the monitor including valves controlled by the control system to flow the particle-containing fluid through the at least one further screen, and the control system determining from the flow the number of particles in the fluid greater than the aperture size of the at least one further screen.

32. A monitor according to claim 31 wherein the first-mentioned screen has an aperture size of 15 μm and the further screen has an apertures size of 100 μm.

33. A monitor according to claim 31 wherein a second further screen is provided, the first-mentioned screen having an aperture size of 15 μm, the first further screen having an aperture size of 100 μm and the second further screen having an aperture size of 200 μm.

34. A method of evaluating particulate contaminants in a fluid comprising:

providing a flow of particulate-containing fluid through a screen having apertures of a single predetermined size for filtering particulate contaminants larger than the predetermined size;

determining when the pressure drop across the screen reaches a steady value;

pulsing flow across the screen in alternate reverse and forward directions; and determining from the pulsed flow the number of particles in the fluid greater than the size of the apertures.

35. A method of evaluating particulate contaminants in a fluid comprising:

washing an article with a fluid in a washing chamber, including removing particulate contaminants from the article via the fluid;

stirring the particulate containing fluid in a collection chamber;

flowing particulate containing fluid through a screen having apertures of a single predetermined size; and determining from the flow the number of particles in the fluid greater than the size of the apertures.

36. A method of evaluating particulate contaminants in fluid comprising:

flowing particulate containing fluid through a screen having apertures of a single predetermined size;

determining from the flow the number of particles in the fluid greater than the size of the apertures;

passing the particulate containing fluid through a filter having a pore size smaller than the size of the smallest screen aperture toward a reservoir; and drawing a washing fluid from the reservoir.

37. A contamination monitor comprising:

a chamber for holding a fluid carrying a particulate contaminant;

a screen having apertures of a single predetermined size;

at least one pump for providing a flow of a clean fluid without a particulate contaminant through the screen and for providing a flow of the particulate containing fluid from the chamber through the screen;

a pressure sensing system coupled to the screen to generate a first signal corresponding to the pressure drop across the screen during the clean fluid flow and a second signal corresponding to the pressure drop across the screen during the particulate containing fluid flow; and a control system coupled to the pressure sensing system and the pump to pulse flow across the screen in alternate reverse and forward directions and to determine from the pulsed flow the number of particles in the particulate containing fluid greater than the predetermined size.

38. A contamination monitor comprising:

a chamber for holding a fluid carrying a particulate contaminant, wherein the chamber has a stirring device for stirring the fluid therein;

a screen having apertures of a single predetermined size;

a reservoir;

a pump connected between the chamber and the reservoir to direct the particulate containing fluid from the chamber through the screen toward the reservoir; and a control system for determining from the flow the number of particles in the fluid greater than the predetermined size.

39. A contamination monitor comprising:

a chamber for holding a fluid carrying a particulate contaminant;

a screen having apertures of a single predetermined size;

a reservoir;

a pump connected between the chamber and the reservoir to direct the particulate containing fluid from the chamber through the screen toward the reservoir;

a control system for determining from the flow the number of particles in the fluid greater than the predetermined size; and a spray device arranged to spray the interior of the chamber to wash off particulates as the particulate containing fluid is being pumped from the chamber.

40. A method according to claim 1 and comprising passing the clean fluid to a reservoir, via a filter having a pore size smaller than the size of the smallest screen aperture.

41. A method according to claim 40 wherein the filter has a $\beta \geq 200$ at 1 μm rating.

* * * * *